(12) United States Patent
Crook et al.

(10) Patent No.: US 7,326,405 B2
(45) Date of Patent: *Feb. 5, 2008

(54) COSMETIC COMPOSITIONS

(75) Inventors: Teresa Barbara Crook, Camberley (GB); Alison Fiona Stephens, Cookham (GB)

(73) Assignee: The Procter & Gamble Company, Cincinnati, OH (US)

( * ) Notice: Subject to any disclaimer, the term of this patent is extended or adjusted under 35 U.S.C. 154(b) by 705 days.

This patent is subject to a terminal disclaimer.

(21) Appl. No.: 10/883,505

(22) Filed: Jul. 1, 2004

(65) Prior Publication Data

US 2006/0002868 A1 Jan. 5, 2006

(51) Int. Cl.
*A61Q 17/04* (2006.01)
*A61Q 19/04* (2006.01)
*A61Q 19/00* (2006.01)
*A61K 8/02* (2006.01)

(52) U.S. Cl. .......... 424/59; 424/60; 424/400; 424/40

(58) Field of Classification Search ........ 424/59, 424/60, 400, 401
See application file for complete search history.

(56) References Cited

U.S. PATENT DOCUMENTS 6,531,116 B1  3/2003  Suares et al.

FOREIGN PATENT DOCUMENTS

| CA | 1311688 | 12/1992 |
| DE | 44 41 470 A | 6/1995 |
| EP | 0 456 545 B1 | 11/1991 |
| EP | 0 500 446 B1 | 8/1992 |
| WO | WO 94/04130 A1 | 3/1994 |
| WO | WO 94/13258 A1 | 6/1994 |
| WO | WO 94/22419 A1 | 10/1994 |
| WO | WO 00/62740 A | 10/2000 |
| WO | WO 01/00164 A | 1/2001 |

*Primary Examiner*—Shelley A. Dodson
(74) *Attorney, Agent, or Firm*—Eric T. Addington; John M. Howell; Brian M. Bolam

(57) ABSTRACT

The method of imparting color to skin comprising applying to the skin a cosmetic compositions comprising an alpha-hydroxyaldehyde self-tanning agent and a water-soluble vitamin $B_3$ compound as a self-tanning composition are provided. The cosmetic compositions are useful for imparting a natural, even and durable tan to the skin when topically applied.

11 Claims, No Drawings

COSMETIC COMPOSITIONS

TECHNICAL FIELD

The present invention relates to cosmetic compositions. More specifically, cosmetic compositions are provided comprising a self-tanning agent and a water-soluble vitamin $B_3$ compound. The cosmetic compositions herein provide improved acute skin colour enhancement and more even skin colouring following topical application.

BACKGROUND

A wide variety of cosmetic compositions containing self-tanning agents have been used to increase the pigmentation of the skin. These compositions have been used to create artificial tans, bronzing the skin in a similar fashion to exposure to the sun. Self-tanning agents are believed to generate skin colouration by reacting with amino acids present in the skin to form coloured chromophores, and hence a tan. However, variation in skin amino acid constitution and content between individuals results in wide variation in the colour achieved with a single product. In order to overcome this, it has been suggested to use colour enhancers to even out these differences by supplementing the amino acids naturally present in the skin.

WO 94/04130, WO 94/13258, and WO 94/22419 disclose apparatus and methods for sunless tanning comprising a fluid comprising dihydroxyacetone, and another fluid formulation comprising a colour enhancer comprising respectively, primary amines, secondary polyamines, and amino acids. Whilst these materials work well as colour enhancers, it has been found that they tend to react too quickly with the self tanning agents, thereby not allowing the self-tanning agents to penetrate the cutaneous layer. As a result, the reaction occurs at the surface of the skin, and may consequently wash off the skin.

EP 0,456,545 B1 and EP 0,500,446 B1 disclose a two-component combination for imparting colour to the skin comprising dihydroxyacetone in component (A) and a monohydroxyindole or disubstituted indole derivative respectively, in component (B). Again, these materials do efficiently increase the colour imparted to the skin by such systems, however safety concerns of the use of these materials have prevented their wide-spread use.

It is therefore desirable to provide improved cosmetic compositions for imparting a natural tan to the skin comprising a self-tanning agent and an alternative colour enhancer that reacts with the self-tanning agent to impart an even and durable colour to the skin with limited irritancy or toxicological potential when topically applied.

SUMMARY

According to the present invention, use of a cosmetic composition comprising a water-soluble vitamin B3 compound and an alpha-hydroxyaldehyde self-tanning agent conforming to the formula;

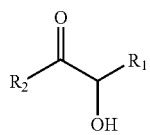

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$ as a self-tanning composition is provided.

DETAILED DESCRIPTION

All weights, measurements and concentrations herein are measured at 25° C. on the composition in its entirety, unless otherwise specified.

Unless otherwise indicated, all percentages of compositions referred to herein are weight percentages of the total composition and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

As used herein, "water-soluble" includes materials that are soluble in water at a level of at least 1 g per 100 ml at 25° C.

The term "safe and effective amount" as used herein, means an amount of an active ingredient high enough to modify the condition to be treated or to deliver the desired skin care benefit, but low enough to avoid serious side effects, at a reasonable benefit to risk ratio within the scope of sound medical judgment. What is a safe and effective amount of the active ingredient will vary with the specific active, the ability of the active to penetrate through the skin or hair, the age, health condition, and skin or hair condition of the user, and other like factors.

As used herein, "cosmetically acceptable" means that ingredients which the term describes are suitable for use in contact with the skin or hair of humans and lower animals without undue toxicity, incompatibility, instability, irritation, allergic response and the like.

As used herein, the term "self-tanning composition" includes compositions that impart colour to the skin using artificial means, preferably chemical means. This term includes compositions that produce an artificial tan similar to that generated to prolonged exposure to solar radiation, and also those compositions that impart a slight colouration to the skin that are not readily recognised as an artificial tan, but rather generate a subtle colour on the skin that makes the skin appear healthier.

According to the present invention, use of a cosmetic composition comprising a water-soluble vitamin $B_3$ derivative and an alpha-hydroxyaldehyde self-tanning agent as a self-tanning composition is provided. It has surprisingly been found tat the combination of an alpha-hydroxyaldehyde self-tanning agent and a water-soluble vitamin $B_3$ derivative synergistically act to impart an improved artificial tan to the skin following topical application. It has previously been demonstrated that vitamin $B_3$ compounds deliver excellent benefits to the skin with regards to repairing skin barrier function. Vitamin $B_3$ compounds have been shown to have a breadth of cutaneous benefits, due to their known status as a precursor of nicotinamide cofactors such as NAD(H), NADP(H). The known benefits of niacinamide include upregulation of sphingolipid synthesis, including those ceramides critical to the formation of the lipid bilayer and so stratum corneum barrier integrity. It has now surprisingly been found that the vitamin $B_3$ compounds or derivatives when applied simultaneously or applied successively with a self-tanning agent result in the generation of an even and rich skin colour on the skin, that is durable. Furthermore, the vitamin $B_3$ compounds are known to be safe and effective when applied topically, with little or no irritancy or toxicological effects. The reaction of vitamin $B_3$ compounds with self-tanning agents is surprising as it was thought that these materials would not take part in a nucleophilic reaction with the self-tanning agent. Without wishing to be bound by theory, it was believed that the nitrogen present in the benzene ring structure, being a tertiary amine, would be highly stable, and therefore not react with the self-tanning agent. However, without wishing to be bound by theory, it is now believed that it is important that the nitrogen present in a benzene ring can delocalise charge and so form intermediate, reactive Schiff base intermediates with the self-tanning agents herein. The formation of the Schiff base intermediates increases the reactivity of the system as increased levels of these intermediates allows a reaction with amino acids present in the skin that, ordinarily, it would not react with to a great extent. Thus, a greater range of amino acids are available for colour generation. Accordingly, the present invention provides a use of the cosmetic compositions herein for increasing the potential of the skin's amino acids to generate colour.

In order to achieve this, the nitrogen present in the benzene ring structure has a sufficiently low pKa such that, at the pH of compositions comprising the self-tanning agents (typically from 3.0 to 5.5), at least 10%, of the vitamin $B_3$ compound remains un-protonated. Preferably, the vitamin $B_3$ compound or its derivatives have a pKa of the tertiary amine of less than 5, preferably less than 4.5. For example, the pKa of the tertiary amine of niacinamide is 3.54.

In addition, it has surprisingly been found that the cosmetic compositions herein are useful for providing controlled and enhanced colouration of the skin. As used herein, the term "controlled colouration" means that the degree of colouration imparted by the cosmetic composition has less variation both inter- and intra-individual, such that the predictability of the skin colouration is improved. Inter-individual variation in colour generation is linked to different people having different levels of the most reactive amino acids in their skin. Increasing the reaction potential of other amino acids evens out these differences between individuals. As used herein, the term "enhanced colouration" means that less alpha-hydroxyaldehyde self-tanning agent is required to provide the same amount of colouration on the skin. Without wishing to be bound by theory, this is believed to be due to the improved reactivity spectrum of the alpha-hydroxyaldehyde self-tanning agent when combined with a water-soluble vitamin $B_3$ compound, such that the two combine to act synergistically in providing colouration to the skin.

Furthermore, it is believed that the highly stable nature of the tertiary amine results in the reaction with the self-tanning agent progressing slowly when topically applied, enabling the vitamin $B_3$ compound to be absorbed by the skin to a significant extent. This is believed to result in the formation of coloured chromophores throughout the cutaneous layer, and consequently a more durable tan is created. Consequently, according to the present invention, a use of the cosmetic compositions herein for improving the wear and/or durability of the artificial tan is provided.

Further still, it has surprisingly been found that the tan or colouration generated on the skin following the use of the cosmetic composition according to the present invention is more even. By this is meant that the skin has a more even colouration, with a reduction in the formation of patches of skin that are either too heavily coloured, or too lightly coloured. In addition, it has been found that the synergistic action of the combination herein also reduces the streaks sometimes associated with self-tanning compositions, where the skin is unevenly coloured due to uneven application of the self-tanning agent to the skin.

A wide range of quantities of the compositions of the present invention can be employed to provide a skin appearance and/or feel benefit. Quantities of the present compositions, which are typically applied per application, are, in mg composition/$cm^2$ skin, from about 0.1 mg/$cm^2$ to about 20 mg/$cm^2$. A particularly useful application amount is about 0.5 mg/$cm^2$ to about 10 mg/$cm^2$. Preferably, the vitamin $B_3$ compound or its derivatives are topically applied either simultaneously or successively with a self-tanning agent as defined herein.

According to the present invention, the cosmetic composition comprises a self-tanning agent. As used herein, the term "self-tanning agent" includes alpha-hydroxy aldehydes and ketones such as dihydroxyacetone and structurally related compounds. This definition includes all such agents that are similarly useful in producing or inducing the artificial tanning process in human skin. Accordingly, the compositions of the present invention comprise an alpha-hydroxy aldehyde or ketone of the formula (I):

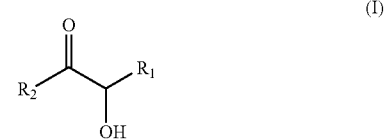

(I)

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$. Dihydroxyacetone (DHA) itself may be represented by the following general structural formula:

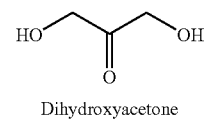

Dihydroxyacetone

A number of other compounds are already known in the art as capable of producing or inducing the same artificial tanning process in human skin as is produced or induced by DHA. Some of these are structurally similar to DHA, and include the following:

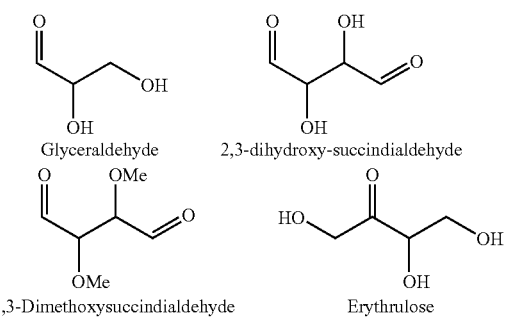

Glyceraldehyde
2,3-dihydroxy-succindialdehyde
2,3-Dimethoxysuccindialdehyde
Erythrulose

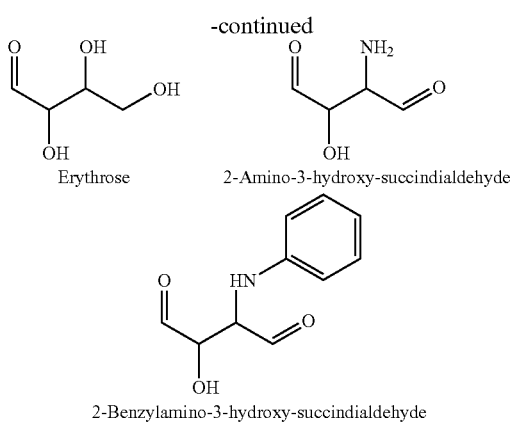

Erythrose

2-Amino-3-hydroxy-succindialdehyde

2-Benzylamino-3-hydroxy-succindialdehyde

Preferably, the self-tanning agent comprises DHA, erythrulose, or mixtures thereof, more preferably DHA. Preferably the compositions of the present invention comprise from 0.01% to 20% of the self-tanning agent by weight of the total composition. More preferably, the compositions of the present invention comprise from 0.05% to 15%, more preferably still from 0.1% to 7%, and even more preferably from 0.1% to 5% of the self-tanning agent by weight of the total composition.

The cosmetic compositions according to the present invention also comprise a water-soluble vitamin $B_3$ compound or its derivatives. As used herein, "vitamin $B_3$ compound" includes compounds having the formula (II):

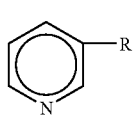

(II)

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. Exemplary derivatives of the foregoing water-soluble vitamin $B_3$ compounds include nicotinyl amino acids, nicotinyl alcohol esters of carboxylic acids, nicotinic acid N-oxide and niacinamide N-oxide. Preferably, the compositions herein comprise niacinamide. Without wishing to be bound by theory, it is believed that the oil-soluble vitamin $B_3$ compounds are not able to react with the self-tanning agents herein to produce coloured chromophores when topically applied, as they are not available in the aqueous phase to take part in the reaction.

Preferably the cosmetic compositions herein comprise from 0.1% to 10%, more preferably from 0.5% to 5% vitamin $B_3$ compound or derivative by weight of the total composition.

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

The cosmetic compositions of the present invention may additionally comprise a skin care active. Skin care actives suitable for use herein comprise panthenol and its derivatives, retinoids and their derivatives, salicylic acid or its derivatives, humectants, amino acids and their derivatives, vitamin C and its derivatives or mixtures thereof. Skin care actives are useful for providing visual improvements in skin appearance or condition following multiple topical applications of the composition to the skin. This "chronic" benefit is particularly desirable as it evens the texture of skin and so increases skin sheen by providing a desquamatory, keratolytic and rejuvenating effect and/or moisturization. The compositions provide long-term visual benefits in conjunction with immediate improvement of skin appearance imparted by the self-tanning agent and the vitamin $B_3$ colour enhancer.

The skin care active may comprise panthenol or its derivatives. The panthenol and its derivatives include D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex. More preferably, the composition herein comprises panthenol. The panthenol or its derivative is preferably used in an amount of from about 0.1% to about 5%, more preferably from about 0.2% to about 3%.

A further class of skin care actives useful herein comprises retinoids. As used herein, "retinoid" includes all natural and/or synthetic analogs of Vitamin A or retinal-like compounds which possess the biological activity of Vitamin A in the skin as well as the geometric isomers and stereoisomers of these compounds. The retinoid is preferably retinal, including retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell U.S. Pat. No. 5,124,356, issued Jun. 23, 1992 to Purcell et al.; and Reissue 34,075, issued Sep. 22, 1992 to Purcell et al. Preferred retinoids comprise retinol, retinyl palmitate, retinyl acetate, retinyl proprionate, retinal or mixtures thereof. More preferred are retinol, retinyl palmitate, or mixtures thereof.

The compositions of this invention may contain a safe and effective amount of the retinoid. The compositions preferably contain from about 0.005% to about 2%, more preferably 0.01% to about 2%, retinoid.

Another class of skin care active according to the present invention comprises humectants. Suitable humectants useful herein include poly-hydric alcohols, sodium 2-pyrrolidone-5-carboxylate (NaPCA), amino acids and derivatives, guanidine; glycolic acid and glycolate salts (e.g. ammonium and quaternary alkyl ammonium); lactic acid and lactate salts (e.g. ammonium and quaternary alkyl ammonium); other alpha hydroxy acids such as malic acid, aloe vera in any of its variety of forms (e.g., aloe vera gel); hyaluronic acid, precursors and derivatives thereof (e.g., glucosamine and salt derivatives such as sodium hyaluronate); lactamide monoethanolamine; acetamide monoethanolamine; urea; and mixtures thereof. Preferred for use in the compositions of the present invention are polyhydric alcohols.

Suitable polyhydric alcohols for use herein include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), trimethylol propane, neopentyl glycol, glycerine, ethoxylated glycerine and propoxylated glycerine. Preferred polyhydric alcohols of the present invention are polyhydric alcohols with 3 to 9 carbon atoms in the molecule. Examples include glycerine, butylene glycol, propylene glycol, dipropylene glycol, polyethylene glycol and derivatives thereof, hexane triol, ethoxylated glycerine and propoxylated glycerine, and mixtures thereof. More preferred for use in the present invention is glycerin. The compositions of the present invention comprise from about 5% to about 40% polyhydric alcohol, preferably from about 8% to about 15% by weight of the composition.

A further class of humectants are the amino acids and their derivatives. Suitable amino acids for use herein include both D- and L-isomers of naturally occurring amino acids. Suitable examples include L-isomers of serine, alanine, proline and hydroxyproline Another skin care active suitable for use herein comprises salicylic acid or its derivatives. Salicylic acid derivatives include any 2, 3 or 4-OR substituted benzoic acid compound having the formula (III):

(III)

wherein R is selected from $C_1$-$C_6$ alkyl or $C_1$-$C_6$ acyl, preferably wherein R is selected from $C_2$-$C_3$ alkyl or $C_2$-$C_3$ acyl. Preferably, the compositions herein comprise salicylic aid. Preferably, the cosmetic kit of the present invention comprises up to 2% salicylic acid or its derivatives, more preferably from 1% to 2% by weight of the total composition.

Another skin care active suitable for use in the compositions according to the present invention comprises a vitamin C compound. Vitamin C compounds include water-soluble ascorbic acid salts and esters thereof. Vitamin C compounds are particularly useful as skin lightening agents. Suitable examples include magnesium ascorbyl phosphate and the sodium salt of the monophosphate ester of ascorbic acid, commercially available from Roche Vitamins Europe Ltd as Stay-C 50™.

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

The cosmetic compositions of the present invention may additionally comprise transition metal oxides. These materials may be pigmentary or sunscreen grades. Non-limiting examples include the Prestige range of silver and gold by Eckart and Flamenco Summit Range such as Flamenco Summit Red, by Engelhard. Where present, the transition metal oxides are typically present at levels of from 0.01% to 20%, more preferably from 0.5% to 10% by weight of the total composition.

Preferably the pH of the cosmetic composition is adjusted to limit the degradation of the self-tanning agents. Preferably, the pH of the composition of the present invention is less than 6.0, more preferably from 2.0 to 5.5, more preferably still from 3.0 to less than 5, in order to stabilise the self-tanning agent therein.

The cosmetic composition herein comprises a safe and effective amount of a dermatologically acceptable carrier. Preferred carriers comprise an emulsion comprising a hydrophilic phase and a hydrophobic phase. As is well known to one skilled in the art, the hydrophilic phase will be dispersed in the hydrophobic phase, or vice versa, to form respectively hydrophilic or hydrophobic dispersed and continuous phases, depending on the composition ingredients. The emulsion may be or comprise (e.g., in a triple or other multi-phase emulsion) an oil-in-water emulsion or a water-in-oil emulsion such as a water-in-silicone emulsion. The compositions herein are preferably in the form of a water-in-oil or oil-in-water emulsion, more preferably an oil-in-water emulsion. The total level of oil phase components in the compositions of the invention is typically from 0.1% to 60%, preferably from 1% to 30%, more preferably from 3% to 20% and more preferably still from 5% to 15% by weight of the total composition.

The hydrophilic phase can comprise water, or a combination of water and one or more water soluble or dispersible ingredients. Hydrophilic components comprising a substantial amount of water are preferred. The composition preferably comprises from about 10% to about 95% of the hydrophilic diluent, more preferably 30% to 85%.

In preferred embodiments, the oil phase preferably comprises oily materials such as a natural or synthetic oils selected from mineral, vegetable, and animal oils, fats and waxes, fatty acid esters, fatty alcohols, fatty acids and mixtures thereof. Preferred for use herein are for example, saturated and unsaturated fatty alcohols such as behenyl alcohol, cetyl alcohol and stearyl alcohol and hydrocarbons such as mineral oils or petrolatum.

The oily phase may further comprise oil-soluble skin care actives. Non-limiting examples of oil-soluble skin care actives suitable for use herein include ceramides, cholesterols, fatty acids, vitamin E or its derivatives, oil-soluble vitamin $B_3$ compounds, or mixtures thereof. Another oil-soluble skin care active suitable for use herein comprise the oil-soluble vitamin $B_3$ compounds including "non-vasodilating" esters of nicotinic acid, examples of which include tocopherol nicotinate. As used herein, the term "non-vasodilating" means that the ester does not commonly yield a visible flushing response after application to the skin in the compositions of interest.

The present compositions may further comprise a silicone phase. The silicone phase can comprise one or more silicone components such as silicone fluids, gums, and mixtures thereof. The, or each, silicone phase generally comprises from 0.1% to 20%, preferably from 0.2% to 10%, more preferably from 0.3% to 5%, of the composition.

The topical compositions of the present invention preferably comprise emollient materials including branched chain hydrocarbons having an weight average molecular weight of from 100 to 15,000. Suitable branched chain hydrocarbons for use herein include isododecane, isohexadecane, isoeicosane, isooctahexacontane, isohexapentacontahectane, isopentacontaoctactane, and mixture thereof. A further emollient suitable for use in the composition of the present invention is petrolatum. The emollient material is preferably present in the compositions at a level of from about 0.1% to about 10%.

The present compositions herein may comprise an emulsifier and/or surfactant, generally to help disperse and suspend the discontinuous phase within the continuous phase. Known or conventional surfactants can be used in the composition, provided that the selected agent is chemically and physically compatible with essential components of the composition, and provides the desired characteristics. The compositions of the present invention preferably comprise from 0.05% to 15% of a surfactant or mixture of surfactants. The exact surfactant or surfactant mixture chosen will depend upon the pH of the composition and the other components present. Surfactants suitable for use herein include non-ionic, cationic, anionic, zwitterionic, amphoteric surfactants, or mixtures thereof, preferably non-ionic surfactants.

The compositions hereof, and especially the emulsions hereof, may contain a structuring agent. Structuring agents are particularly preferred in the oil-in-water emulsions of the present invention. Preferred for use herein are for example, saturated and unsaturated fatty alcohols such as behenyl alcohol, cetyl alcohol and stearyl alcohol.

The compositions of the present invention can also comprise a thickening agent, preferably from about 0.1% to about 5%, more preferably from about 0.1% to about 3%, and most preferably from about 0.25% to about 2%, of a thickening agent. Non-limiting examples of thickening agents suitable for use herein include cross-linked acrylate copolymers, hydroxyalkylacrylate copolymers, polyacrylamide polymers, natural gum thickeners, or mixtures thereof.

The compositions of the present invention may optionally include particulate materials. Particulate materials suitable herein include materials that are insoluble in both water and oil with a median particle size of from 1 µm to 50 µm. Suitable particulate materials are organic or organosilicone or inorganic. Representative commercially available examples of useful particulate materials herein are Microthene FN510™, Tospearl 145™, Orgasol 2002™, Nylonpoly WL10™, Dry Flo™ or mixtures thereof. The compositions of the present invention can comprise from about 0.1% to about 5% by weight of particulate materials.

A further optional component may comprise sunscreening agents. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206-38269, Aug. 25, 1978.

Due to the fact that the self-tanning agent and the vitamin $B_3$ compound react with one another, the cosmetic composition of the present invention may be formulated as a kit comprising at least two components (a) and (b) that are stored separately, and intended to be mixed at the time of use, or to be applied successively to the skin, with component (a) comprising the self-tanning agent, and component (b) comprising the vitamin $B_3$ compound. For the purposes of the present invention, the at least two components are given the designations component (a) and component (b). These designations are not intended to be limiting, such as for example indicating the order of application of the components. The designations are intended to indicate the two separate components and the constituents thereof. The two components (a) and (b) may be dispensed and applied to the skin at a ratio by weight of from 1:99 to 99:1. Preferably, the components are dispensed and applied to the skin at a ratio of from 20:80 to 80:20, more preferably from 40:60 to 60:40. As used herein, the term "applied successively" means that the components of the present invention are dispensed and applied one after the other, the order of dispensing not being limited, such that component (a) can be dispensed either before or after component (b). Furthermore, the at least two components of the present invention may be dispensed and applied successively without directly following on from one another temporally, such that other components may be dispensed and applied at points before or after the first application of one of the at least two components, provided that the successive application of components (a) and (b) occurs within less than 2 hours of each other, preferably less than 1 hour, more preferably less than 30 minutes.

In order to facilitate the separate storage of the at least two components, the cosmetic composition of the present invention may be stored in a package for separately storing the at least two components. These packages are typically known to one skilled in the art as "dual chamber" packages. Non-limiting examples of packaging suitable for use herein include an integral package comprising at least two compartments divided by separating means, one compartment comprising component (a) and the other comprising component (b). The separating means for keeping the two components apart may comprise a physical barrier such as a septum, or other similar barrier that prevents mixing of the two components from the at least two compartments known to those skilled in the art. Non-limiting examples of such packages include tubes comprising an exterior wall defining the outer surface of the tube and an inner void, and an interior septum, dividing the inner void into two compartments along its longitudinal axis such that the two components are kept separate until dispensed. Non-limiting examples of commercially available integral dual chamber packages comprising two separated compartments include dual chamber packages available from Airspray and Megaplast, and dual chamber tubes available from Cebel.

The cosmetic composition of the present application may be used in the form of a kit comprising at least two packages, with component (a) being stored in one package, and component (b) in the other. The packages may be of similar design, or of different design. As is known to those skilled in the art, the package design will somewhat depend upon the product form, such that lotions and creams may be packaged in flexible or rigid-walled packages, whilst aerosol compositions typically are stored in rigid-walled, pressurised packages.

The cosmetic compositions of the present invention may be made into a wide variety of product forms such as are known in the art. These include, but are not limited to, lotions, creams, gels, sticks, sprays, ointments, pastes, mousses, aerosols and cosmetics (e.g., foundations, eye-makeup, pigmented or non-pigmented lip treatments, e.g., lipsticks, and the like). As previously indicated, it may be preferable to formulate the cosmetic composition of the present invention as two separated components intended to be dispensed simultaneously and be mixed at the time of use, or to be applied sequentially, with one component being applied, followed by another.

Where the two components are to be applied simultaneously, it is preferable that they are made in compatible product forms. Alternatively, where the two components are to be applied sequentially, the at least two components may be made in any combination of product forms known to one skilled in the art.

EXAMPLES

Unless otherwise stated, all the following examples are formulated such as to be mixed at a ratio of 50:50 during application. Each of components (a) and (b) have had their total ingredients summed to 100%.

Examples 1-3

Moisturising Cream Kits

| INGREDIENTS | EXAMPLE 1 Component (a) (w/w %) | EXAMPLE 1 Component (b) (w/w %) | EXAMPLE 2 Component (a) (w/w %) | EXAMPLE 2 Component (b) (w/w %) | EXAMPLE 3 Component (a) (w/w %) | EXAMPLE 3 Component (b) (w/w %) |
|---|---|---|---|---|---|---|
| DEIONISED WATER | QS | QS | QS | QS | QS | QS |
| GLYCERINE | 10.0 | 10.0 | 5.0 | 5.0 | 15.0 | 15.0 |
| NIACINAMIDE | 3.5 | — | 5.0 | — | 2.0 | — |
| PANTHENOL | 0.5 | — | — | — | 2.0 | — |
| VITAMIN E ACETATE | 0.25 | 0.25 | 0.25 | 0.25 | 0.25 | 0.25 |
| ISOHEXADECANE | 3.0 | 3.0 | 3.0 | 3.0 | 3.0 | 3.0 |
| ISOPROPYL ISOSTEARATE | 1.50 | 1.50 | 1.50 | 1.50 | 1.3 | 1.50 |
| COCO-NUT OIL FRACTIONATED | 0.2 | 0.2 | 0.2 | 0.2 | — | — |
| PETROLATUM | 2.0 | 2.0 | 2.0 | 2.0 | 2.0 | 2.0 |
| SIMUGEL NS[3] | — | 1.5 | — | 1.5 | — | 2.0 |
| LUVIGEL EM[4] | 2.0 | — | — | — | 2.5 | — |
| SEPIGEL 305[5] | — | — | 1.5 | — | — | — |
| XANTHAN GUM | 0.1 | 0.1 | 0.1 | 0.2 | 0.1 | 0.2 |
| SORBITAN STEARATE | — | — | — | — | 0.9 | — |
| STEARYL ALCOHOL | 0.6 | 0.6 | 0.6 | 0.6 | 0.55 | 0.6 |
| CETYL ALCOHOL | 0.5 | 0.5 | 0.5 | 0.5 | 0.8 | 0.5 |
| BEHENYL ALCOHOL | 0.4 | 0.4 | 0.4 | 0.4 | — | 0.4 |
| PEG-100 STEARATE | 0.1 | 0.1 | 0.1 | 0.1 | 0.1 | 0.1 |
| STEARIC ACID | 0.1 | — | 0.1 | — | 0.1 | — |
| SODIUM HYDROXIDE | 0.01 | — | 0.01 | — | 0.04 | — |
| EMULGADE[6] | 0.2 | 0.2 | 0.2 | 0.2 | 0.2 | 0.2 |
| NYLONPOLY WL10[7] | — | 1.0 | — | 1.0 | — | 1.0 |
| DRY FLO PLUS[8] | 0.5 | 1.0 | 0.5 | 1.0 | 0.5 | 1.0 |
| MICROTHENE[9] | — | — | 0.5 | — | — | — |
| FLAMENCO SUMMIT RED[10] | 2.0 | — | — | — | 2.0 | — |
| TITANIUM DIOXIDE | — | — | 0.5 | — | — | — |
| DHA[11] | — | 1.5 | — | 1.8 | — | 5.0 |
| ERYTHRULOSE[12] | — | — | — | 0.6 | — | — |
| ETHYL PARABEN | 0.15 | 0.15 | 0.15 | 0.15 | 0.15 | 0.15 |
| PROPYL PARABEN | 0.07 | 0.07 | 0.07 | 0.07 | 0.07 | 0.07 |
| DISODIUM EDTA | 0.1 | 0.1 | 0.1 | 0.1 | 0.1 | 0.1 |
| BENZYL ALCOHOL | 0.25 | 0.25 | 0.25 | 0.25 | 0.25 | 0.25 |
| DC 1503 | 1.0 | 1.0 | 1.0 | 1.0 | 1.0 | 1.0 |
| PERFUME | 0.2 | 0.2 | 0.2 | 0.2 | 0.2 | 0.2 |

[1]SK Influx: Supplied by Goldschmidt AG, Goldschmidtstrasse 100, D-45127 Essen, Germany.
[2]Tocopherol Nicotinate: Supplied by Ennagram UK Ltd, Edelman House, 1238 High Road, Whetstone, London.
[3]Simugel NS: Supplied by Seppic, 75 Quai D'Orsay, Paris
[4]Luvigel EM: BASF Plc, PO Box 4-Earl Road, Cheadle Hulme, Cheshire SK8 6QG
[5]Sepigel 305: Supplied by Seppic, 75 Quai D'Orsay, Paris
[6]Emulgade: Supplied by Cognis Deutchland GmbH, Paul-Thomas Strasse 56, D-40551 Dusseldorf, Germany.
[7]Nylonpoly WL10: Supplier Optima Chemicals, Unit 17, Chiltern Business Village, Arundel Road, Uxbridge, Middlesex, UB8 2SN
[8]Dry Flo: Supplied by National Starch Chemical Company, 10, Finderne Avenue, Bridgewater, NJ 08807, USA
[9]Microthene: Supplied by Equistar Chemicals, 1221 McKinney Street, Suite 700, Houston, TX 77252-2583
[10]Flamenco Summit Red: Supplied by Engelhard P&A Europe, Emrikweg 18, NL-2031 BT Haarlem, Netherlands.
[11]DHA: Supplied by Merck GmBH, Frankfurter Strasse 250, 64293 Darmstadt, Germany.
[12]Erythrulose: Supplied by Pentapharm, Engelgasse 109, 4002 Basel, Switzerland.

The compositions are made as follows:

A water phase is prepared by admixing all water-soluble ingredients (including xanthan gum), except DHA and Erythrulose (if included), in water and heating to 80° C. A second premix is prepared by admixing of the oil-soluble ingredients except the silicone oil (DC1503) and heating also to 80° C. The oil phase is added to the water phase and sheared to form an emulsion.

The emulsion is cooled to 60° C. and the polymeric thickener is then added. At 45-50° C. the benzyl alcohol and DC1503, and particles (if included) are added and the resulting product is sheared to ensure particle dispersion, de-agglomeration and homogeneity. The composition can then be cooled to below 40° C. and DHA, Erythrulose (if included) and perfume can be added. The compositions are applied to the skin and an artificial tan is allowed to develop.

Example 4

Disposable Fluid Applicator Kit

The disposable applicator already comprises the fluid to be dispensed, so does not require addition of any fluid prior to use. Example 1 is taken and at least one of the phases is incorporated within a rupturable dosing reservoir capable of containing and dispensing the cream. The second phase may be contained in a similar manner or within an alternative type of reservoir ie. foam etc. The reservoirs are then enclosed within a flow control layer comprising an apertured film to allow the cream to be dispensed onto the skin when pressure is applied. Preferably, additional batting, sponge or foam is added to aid handleability and a fluid impermeable layer incorporated to prevent flow of product onto the hands.

Example 5

Moisturising Gel Kit

| INGREDIENTS | EXAMPLE 5 | |
|---|---|---|
| | Component (a) (w/w %) | Component (b) (w/w %) |
| DEIONISED WATER | QS | QS |
| GLYCERINE | 5.0 | 5.0 |
| NIACINAMIDE | 4.0 | — |
| PANTHENOL | 1.0 | — |
| SIMUGEL NS[3] | 3.0 | 3.0 |
| XANTHAN GUM | 0.2 | 0.2 |
| DHA[11] | — | — |
| ERYTHRULOSE[12] | — | — |
| ETHYL PARABEN | 0.15 | 0.15 |
| PROPYL PARABEN | 0.07 | 0.07 |
| DISODIUM EDTA | 0.1 | 0.1 |
| BENZYL ALCOHOL | 0.25 | 0.25 |
| PERFUME | 0.2 | 0.2 |

The compositions are made as follows:

The gel is made by dissolving the preservatives, niacinamide and DHA (if included) into a glycerine/water and panthenol pre-mix. Mixing should be done with a Lightin' mixer with a 3-blade paddle propeller. When the ingredients have dissolved xanthan gum is added and allowed to hydrate. The polymeric thickener is then added, whilst mixing at a moderate speed, and the gel forms. The product can then be prepared for packaging. The compositions are applied to the skin and an artificial tan is allowed to develop.

Example 6

Line Minimising Moisturiser Kit

| INGREDIENTS | EXAMPLE 6 | |
|---|---|---|
| | Phase 1 (w/w %) | Phase 2 (w/w %) |
| DEIONISED WATER | QS | QS |
| GLYCERINE | 10.0 | 10.0 |
| NIACINAMIDE | 3.5 | — |
| PANTHENOL | 0.5 | — |
| DC9040[13] | 25.0 | 25.0 |
| DC245[14] | 15.0 | 15.0 |
| DC AMS C30 Wax[15] | 3.0 | 3.0 |
| KSG21[15] | 10.0 | 10.0 |
| DHA[11] | — | 2.0 |
| PROPYL PARABEN | 0.25 | 0.25 |
| DISODIUM EDTA | 0.1 | 0.1 |
| PHENOXYETHANOL | 0.25 | 0.25 |
| PERFUME | 0.1 | 0.1 |

[13,14 and 15]Supplied by Dow Corning, Kings Court, 185 Kinds Rd, Reading, Berks, RGI 4EX14.
KSG21: Supplied by Shin Etsu, Bolderweg 32, 1332 AV, Almere, The Netherlands The compositions are made as follows:

A water phase is prepared by admixing all water soluble ingredients, except DHA (if included) and phenoxyethanol, in water and heating to 50° C. Once the phase is clear, it is cooled and the phenoxyethanol and DHA (if included) are added. A second premix is prepared by heating the DC245 to 80° C. When at temperature the wax is added and allowed to melt. Once fully molten the DC9040 is added and the mixture is allowed to cool whilst mixing under low shear continuously. Once below 40° C., the perfume is incorporated in the silicone phase and then the water phase is added and sheared to form an emulsion. The product is then suitable for packing into an appropriate container. The compositions are applied to the skin and an artificial tan is allowed to develop.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of imparting colour to skin comprising applying to the skin a cosmetic composition comprising a water-soluble vitamin $B_3$ compound and an alpha-hydroxy-aldehyde self-tanning agent conforming to the formula;

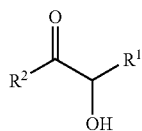

wherein $R^1$ is H, $CH_2OH$, $CHOHCH_2OH$, $CH(OH)CH(=O)$, $CH(OCH_3)CH(=O)$, $CH(NH_2)CH(=O)$, or $CH(NH\text{-}Phenyl)CH(=O)$; and $R^2$ is H or $CH_2OH$ as a self-tanning composition.

2. The method according to claim 1 wherein said self-tanning agent comprises dihydroxyacetone, erythrulose or mixtures thereof.

3. The method according to claim 2 wherein said self-tanning agent comprises dihydroxyacetone.

4. The method according to claim 1 wherein said composition comprises from about 0.01% to about 20% self-tanning agent by weight of the composition.

5. The method according to claim 1 wherein said water-soluble vitamin $B_3$ compound comprises niacinamide.

6. The method according to claim 1 comprising from about 0.1% to about 10% water-soluble vitamin $B_3$ compound or its derivatives by weight of the composition.

7. The method according to claim 1 wherein said composition additionally comprises a skin care active.

8. The method according to claim 7 wherein the skin care active comprises panthenol and its derivatives, retinoids and their derivatives, salicylic acid or its derivatives, humectatns, amino acids and their derivatives, vitamin C and its derivatives or mixtures thereof.

9. The method according to claim 8 wherein said humectant comprises $C_3$ to $C_9$ polyhydric alcohols.

10. The method according to claim 9 wherein said humectant comprises glycerin.

11. The method according to claim 8 comprising from about 5% to about 40% humectant.

\* \* \* \* \*